US009173689B2

(12) United States Patent
Humphreys

(10) Patent No.: US 9,173,689 B2
(45) Date of Patent: *Nov. 3, 2015

(54) RETAINING MECHANISM

(71) Applicant: Warsaw Orthropedics, Inc., Warsaw, IN (US)

(72) Inventor: Kevin Humphreys, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 230 days.

This patent is subject to a terminal disclaimer.

(21) Appl. No.: 13/851,372

(22) Filed: Mar. 27, 2013

(65) Prior Publication Data
US 2013/0218211 A1 Aug. 22, 2013

Related U.S. Application Data

(63) Continuation of application No. 12/970,130, filed on Dec. 16, 2010, now Pat. No. 8,454,667.

(51) Int. Cl.
*A61B 17/80* (2006.01)

(52) U.S. Cl.
CPC ................................. *A61B 17/8042* (2013.01)

(58) Field of Classification Search
CPC .................................................. A61B 17/8042
USPC .................................. 606/289, 294, 295, 296
See application file for complete search history.

(56) References Cited

U.S. PATENT DOCUMENTS

| | | | |
|---|---|---|---|
| 6,306,139 B1 | 10/2001 | Fuentes | |
| 7,306,605 B2 | 12/2007 | Ross | |
| 7,452,370 B2 * | 11/2008 | Anderson | 606/296 |
| 7,727,266 B2 | 6/2010 | Lindemann et al. | |
| 8,821,554 B2 * | 9/2014 | Stanaford et al. | 606/295 |
| 2008/0287999 A1 * | 11/2008 | Markworth | 606/280 |
| 2010/0042159 A1 * | 2/2010 | Butler | 606/286 |

* cited by examiner

Primary Examiner — Nicholas Woodall

(57) ABSTRACT

A retaining mechanism for use in affixing a stratum to bone is disclosed. The retaining mechanism comprises a stratum, a retaining element and a spring element. The stratum comprising a first surface, a second surface, and a hole extending between the first surface and the second surface, wherein the second surface is configured to engage at least a portion of the bone. The retaining element comprises a first position that permits a fastener to be passed through the hole, and a second position that at least partially overlaps the hole. The spring element is configured to engage the stratum and configured to engage the retaining element such that the spring element helps maintain the retaining element in its second position so as to help prevent inadvertent backing out of the fastener after the fastener has been fully inserted into the hole.

20 Claims, 6 Drawing Sheets

RETAINING MECHANISM

CROSS-REFERENCE TO RELATED APPLICATION

This application is a continuation of application Ser. No. 12/970,130, filed on Dec. 16, 2010, now allowed. The contents of this prior application is herein incorporated by reference in its entirety.

FIELD OF INVENTION

The present invention is directed to systems for affixing a stratum to bone.

BACKGROUND

The present disclosure relates to retaining mechanisms, and more particularly, systems for affixing a stratum to bone.

SUMMARY OF THE INVENTION

A retaining mechanism for use in affixing a stratum to bone is disclosed. The retaining mechanism comprises a stratum, a retaining element and a spring element. The stratum comprising a first surface, a second surface, and a hole extending between the first surface and the second surface, wherein the second surface is configured to engage at least a portion of the bone. The retaining element comprises a first position that permits a fastener to be passed through the hole, and a second position that at least partially overlaps the hole. The spring element is configured to engage the stratum and configured to engage the retaining element such that the spring element helps maintain the retaining element in its second position so as to help prevent inadvertent backing out of the fastener after the fastener has been fully inserted into the hole.

Further, a system for affixing stratum to bone is disclosed. The system comprises a retaining mechanism and at least one fastener configured to pass through the hole in the stratum and engage the bone.

DETAILED DESCRIPTION

Figure 1:
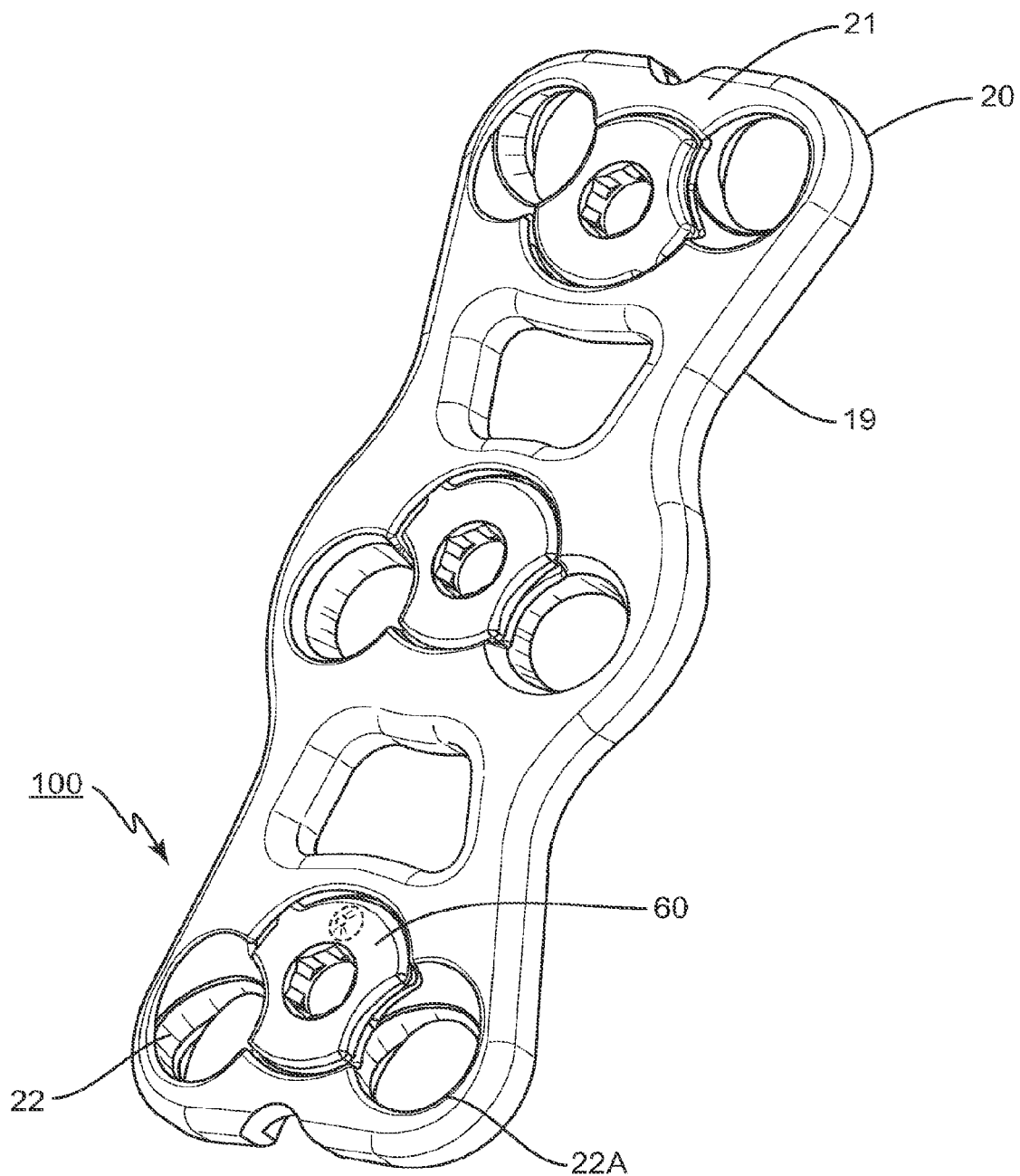
FIG. 1 is an isometric top view of a retaining mechanism for affixing a stratum to bone.

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

FIG. 1 shows an isometric top view of a retaining mechanism 100 for affixing a stratum 20 to bone, for example, to two or more levels of vertebral bodies. As shown in FIG. 1, the stratum 100 is designed for connecting three vertebral bodies (not shown), each vertebral body receiving two fasteners, one fastener through each hole, for example, holes 22 and 22A. As shown in FIG. 1, the stratum 20 may be, for example, a spinal plate for connecting cervical vertebrae by affixing the stratum 20 to the anterior surface of the vertebrae. Further, as shown in the Figures and as described herein, the fasteners may be, for example, screws.

The retaining mechanism 100 comprises a stratum 20, a retaining element 60 and a spring element 30. The stratum 20 comprises a first surface 19, a second surface 21, and six holes (for example, holes 22 and 22A) extending between the first surface 19 and the second surface 21. As shown in FIG. 1, the first surface 19 is configured to engage at least a portion of the bone. The retaining element 60 comprises a first position that permits a fastener to be passed through the hole (for example, hole 22 or 22A), a second position that at least partially overlaps the hole (for example, hole 22 or 22A), and a spring element 30 configured to engage the stratum 20 and configured to engage the retaining element 60 such that the spring element 30 helps maintain the retaining element 60 in its second position so as to help prevent inadvertent backing out of the fastener after the fastener has been fully inserted into the hole (for example, hole 22 or 22A). Note that, as shown in FIG. 1, the stratum contains three retaining mechanisms. One is retaining mechanism 100 and the other two are similar, with each mechanism configured for another bone or bone segment, for example, configured for separate vertebral bodies.

Figure 2:
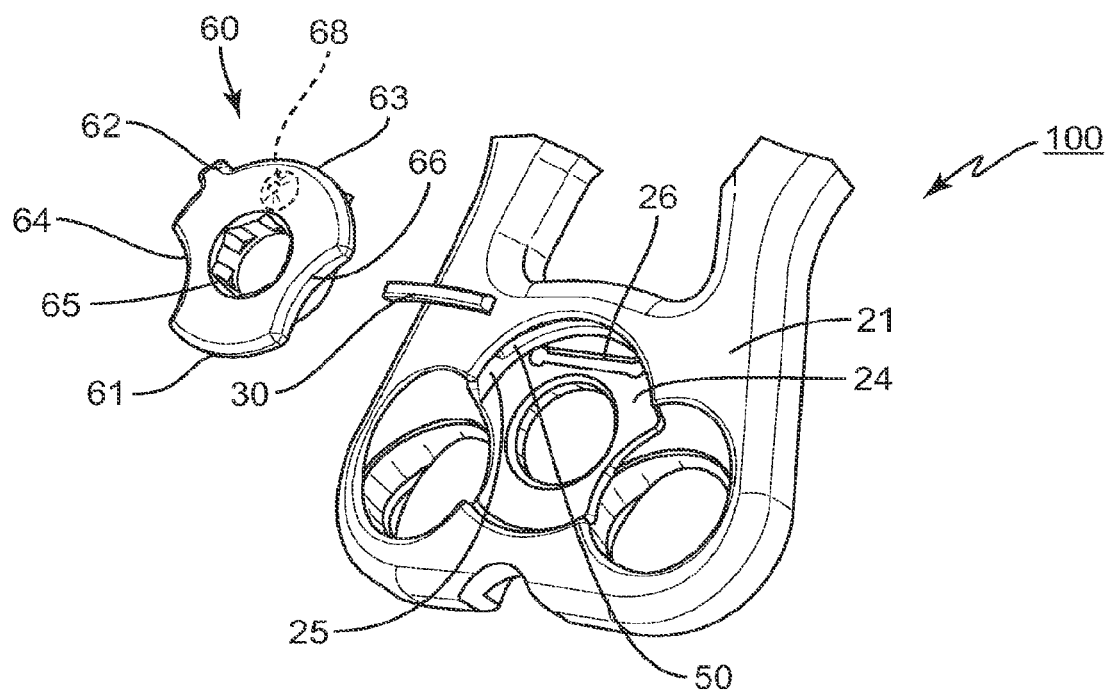
FIG. 2 is a cut-away, exploded, isometric top view of retaining mechanism of FIG. 1.

FIG. 2 shows a cut-away, exploded, isometric top view of retaining mechanism 100 of FIG. 1. As shown in FIG. 2, the stratum 20 is further configured to engage the retaining element 60. As shown in FIG. 2, the second surface 21 of the stratum 20 comprises a first recess 24 configured to engage the retaining element 60. Further, as shown in FIG. 2, the first recess 24 comprises a second recess 26 configured to engage the spring element 30.

In addition, as shown in FIG. 2, the retaining element 60 further comprises a tab 62 and the stratum 20 further comprises a channel 50. As shown in FIG. 2, the tab 62 extends away from a center of the retaining element 60. Further, as shown in FIG. 2, the first recess 24 comprises a sidewall 25 and the sidewall 25 comprises the channel 50. More specifically, as shown in FIG. 2, the channel 50 is what remains after a section of material is removed from the sidewall 25. As shown in FIG. 2, the channel 50 is configured to engage the tab 62 and the tab 62 is configured to engage the channel 50.

In addition, as shown in FIG. 2, the retaining element 60 further comprises a first cut-out 64 and a second cut-out 66. In addition, as shown in FIG. 2, the retaining element 60 further comprises a depression 68 (shown in phantom lines) on its underside, i.e., the side facing the first recess 24 of the stratum 20.

Figure 3:
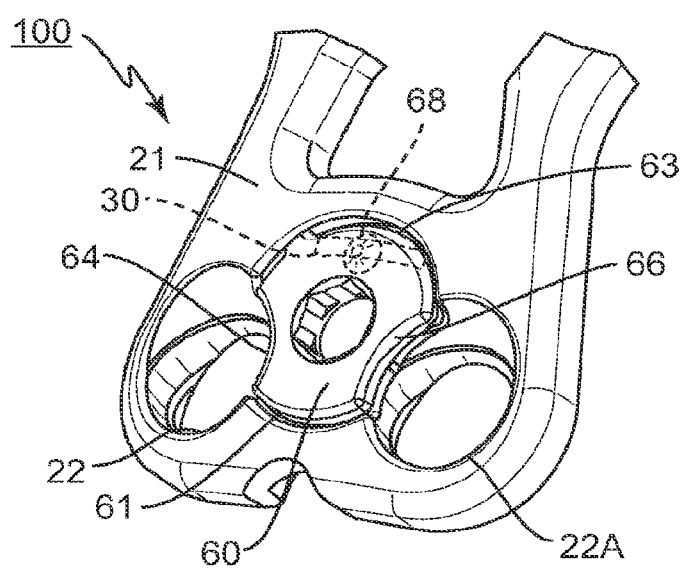
FIG. 3 is a cut-away, isometric top view of the retaining mechanism of FIG. 1.

FIG. 3 shows a cut-away, isometric top view of the retaining mechanism 100 of FIG. 1. As shown in FIG. 3, the retaining element 60 is in its first position, which permits a fastener to be passed through the hole 22 or 22A. Further, as shown in FIG. 3, the depression 68 is positioned and configured to engage the spring element 30 when the retaining element 60 is in its first position.

Figure 4:
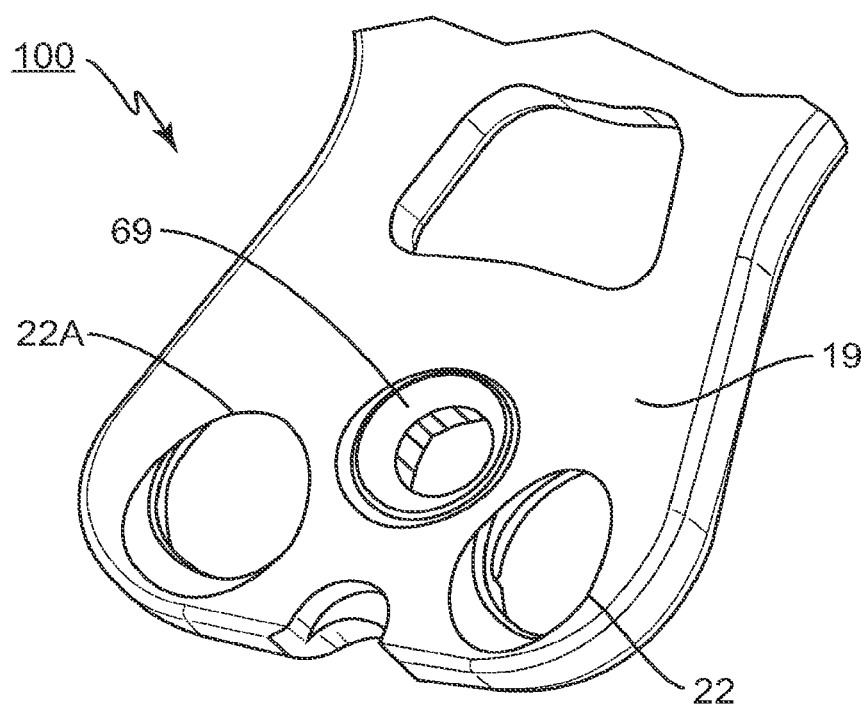
FIG. 4 is a cut-away, isometric bottom view of the retaining mechanism of FIG. 1.

FIG. 4 shows a cut-away, isometric bottom view of the retaining mechanism 100 of FIG. 1. As shown in FIG. 4, the retaining element 60 further comprises a grommet portion 69 situated between holes 22 and 22A. The grommet portion 69 helps the retaining element 60 maintain position affixed to the stratum 20, but also allows the retaining element 60 to rotate, for example, between its first position and its second position.

Figure 5:
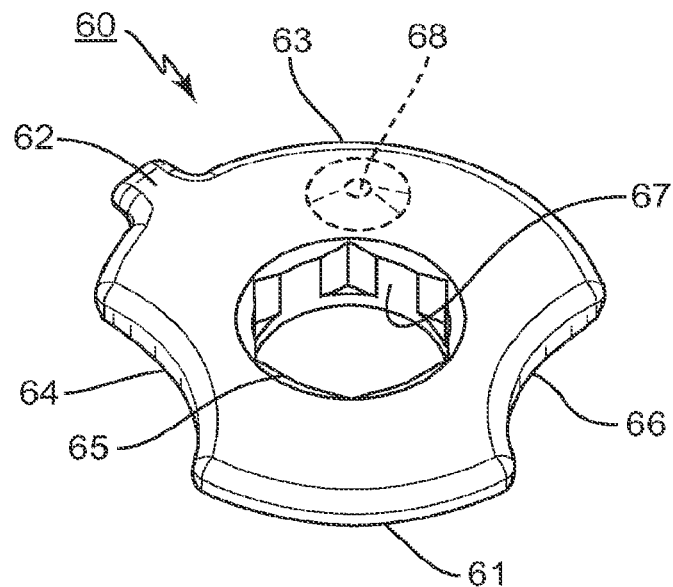
FIG. 5 is an isometric top view of the retaining element of FIG. 1.

FIG. 5 shows an isometric top view of the retaining element 60 of FIG. 1. As shown in FIG. 5, the depression 68 is visible in phantom lines (as well as in other figures) because it is situated on the underside of the retaining element 60. Further, as shown in FIG. 5, the retaining element 60 further comprises a central shaft 67 that passes through the stratum 20. As shown in FIG. 5, at least the top of the central shaft 67 has a hexagonal shape 65. Also, as shown, the central shaft 67 defines a hole through the retaining element 60 and is situated at or near the center of the retaining element 60. As shown, the retaining element 60 may be rotated by, for example, inserting a hexagonal-shaped end of a tool into the central shaft 67 to thereby rotate the retaining element 60 from, for example, its first position to its second position, or vice versa. Note that the central shaft 67 (and corresponding tool) need not have a hexagonal-shape 65, but may be one of a variety of shapes so long as the function of rotating the retaining element 60 can be accomplished. For example, other polygonal shapes such as a square would suffice.

Figure 6:
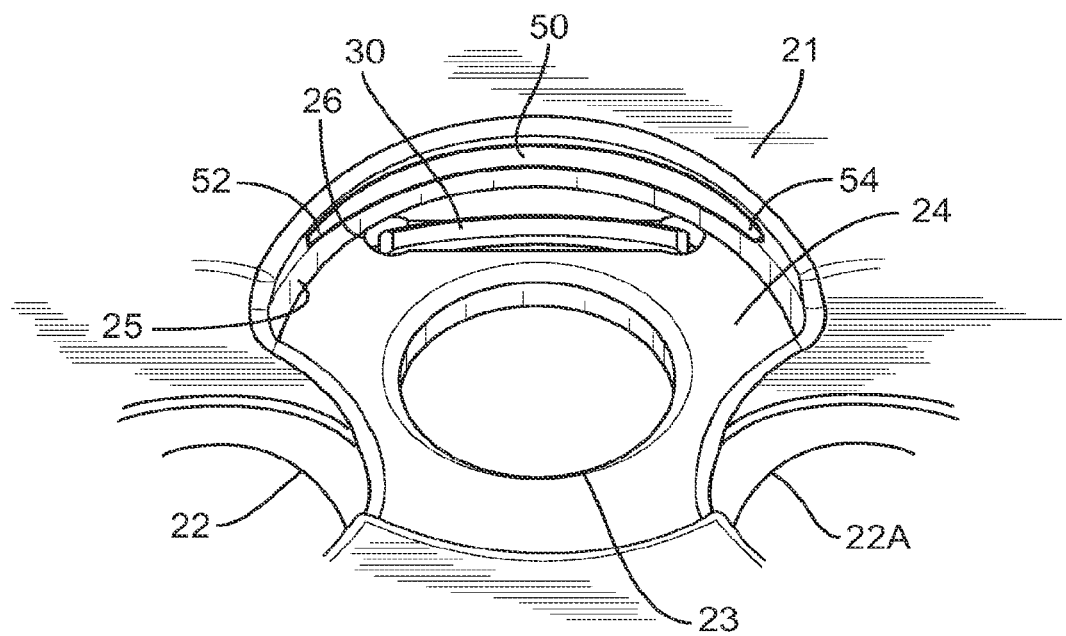
FIG. 6 is a cut-away, isometric top view of the stratum of FIG. 1.

FIG. 6 shows a cut-away, isometric top view of the stratum 20 of FIG. 1. FIG. 6 shows an enlarged view of the first recess 24, the second recess 26, the spring element 30 and the channel 50. As shown in FIG. 6, the stratum 20 further comprises a central hole 23 configured to receive the central shaft 67 of the retaining element 60. Further, as shown in FIG. 6, the channel 50 comprises a first end 52 and a second end 54. When the retaining element 60 is in its first position, the tab 62 is situated at or near the first end of the channel 52. When the retaining element 60 is in its second position, the tab 62 is situated at or near the second end of the channel 54.

Figure 7:
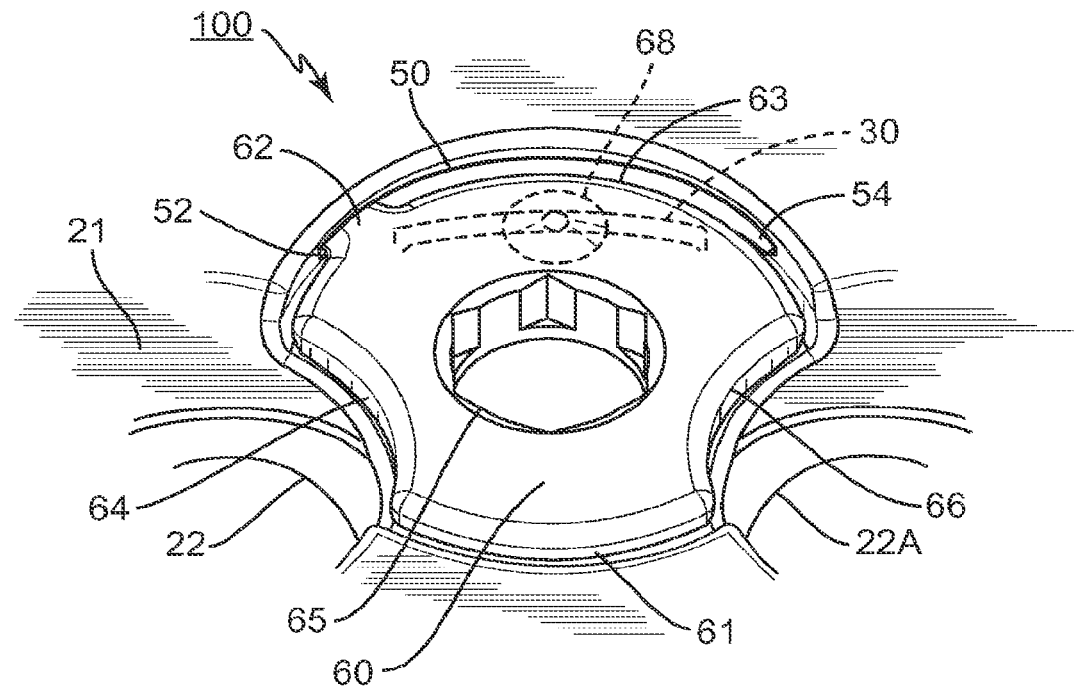
FIG. 7 is a cut-away, isometric top view of the retaining mechanism of FIG. 1.

FIG. 7 shows a cut-away, isometric top view of the retaining mechanism 100 of FIG. 1. Specifically, FIG. 7 shows an enlarged view of the area surrounding the retaining element 60 when it is in its first position. As shown in FIG. 7, when the retaining element 60 is in its first position, the first cut-out 64 and the second cut-out 66 of the retaining element 60 permit first and second fasteners to be passed through the first and second holes 22 and 22A of the stratum 20, respectively. Further, as shown in FIG. 7, when the retaining element 60 is in its first position, the depression 68 on the underside of the retaining element 60 engages the spring element 30. In this way, depression 68 is intended to at least partially relieve forces exerted on the spring element 30 when the retaining element 60 is in its first position.

Figure 8:
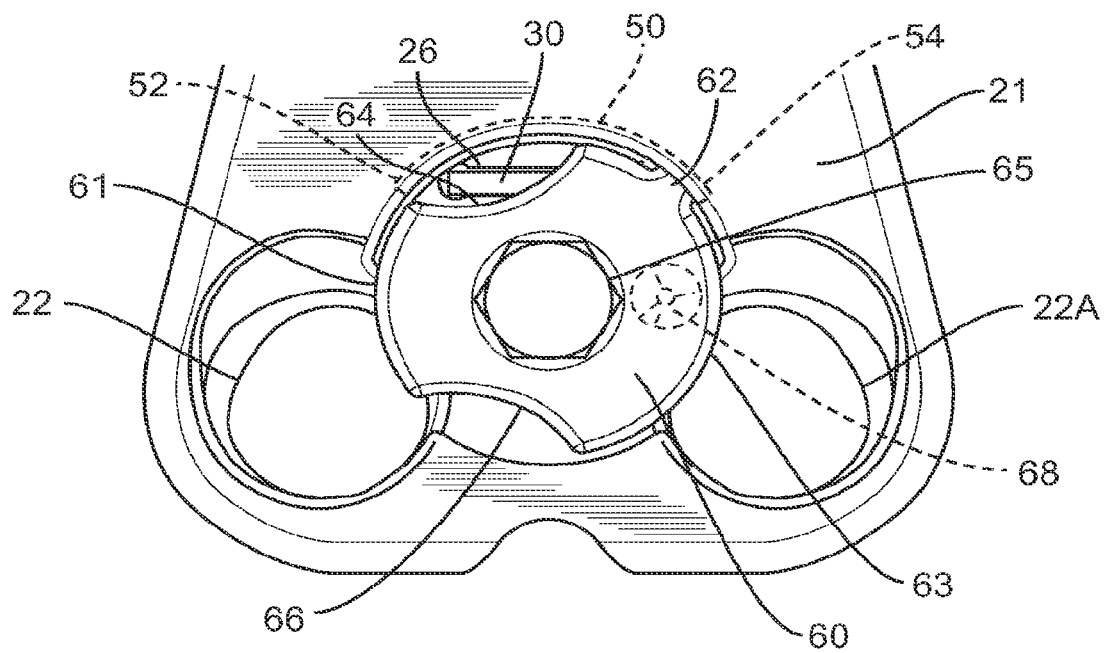
FIG. 8 is another cut-away, isometric top view of the retaining mechanism of FIG. 1.

FIG. 8 shows another cut-away, isometric top view of the retaining mechanism 100 of FIG. 1. Specifically, FIG. 8 shows an enlarged view of the area surrounding the retaining element 60 when it is in its second position. As shown in FIG. 8, the retaining element 60 further comprises a first blocking portion 61 and a second blocking portion 63. The first cut-out 64 is situated between the first blocking portion 61 and the second blocking portion 63, and the second cut-out 66 is situated opposite the first cut-out 64, and similarly, between the first blocking portion 61 and the second blocking portion 63. As shown in FIG. 8, the when the retaining element 60 is in its second position, the first blocking portion 61 and the second blocking portion 63 of the retaining element 60 partially overlap the first and second holes 22 and 22A of the stratum 20, respectively, so as to prevent inadvertent backing out of fasteners after they have been fully inserted into the first and second holes 22 and 22A. Further, as shown in FIG. 8, when the retaining element 60 is in its second position, the first cut-out 64 engages the spring element 30 so as to help maintain the retaining element 60 in its second position. When the retaining element 60 is in its second position, the spring element 30 is less stressed than when the retaining element 60 rotates between its first and second positions, but applies enough pressure against the first cut-out 64 to help maintain the retaining element 60 in its second position.

Figure 9:
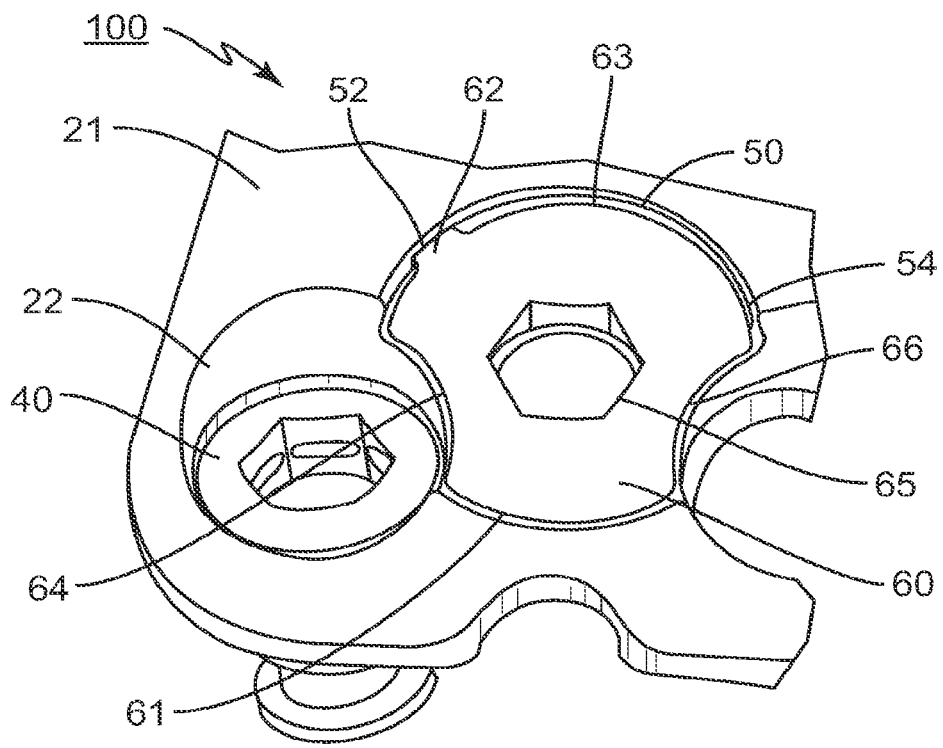
FIG. 9 is a cut-away, isometric top view of a system for affixing the stratum of FIG. 1 to bone.

FIG. 9 shows a cut-away, isometric top view of a system for affixing the stratum 20 of FIG. 1 to bone. As shown in FIG. 9, system comprises the retaining mechanism 100 and a fastener 40 configured to pass through the hole 22 and engage the bone. Specifically, FIG. 9 shows an enlarged view of the area surrounding the retaining element 60 when it is in its first position. As shown in FIG. 9, when the retaining element 60 is in its first position, the first cut-out 64 and the second cut-out 66 of the retaining element 60 permit the first fastener 40 and a second fastener to be passed through the first and second holes 22 and 22A of the stratum 20, respectively. Further, as shown in FIG. 9, when the retaining element 60 is in its first position, the depression 68 on the underside of the retaining element 60 engages the spring element 30.

Figure 10:
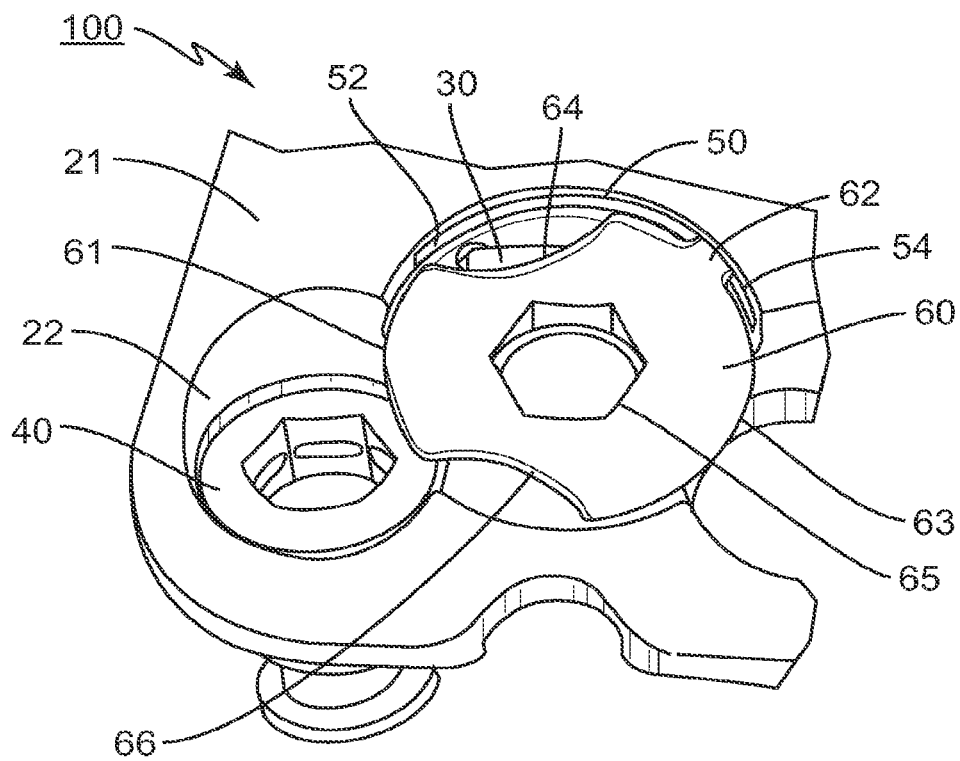
FIG. 10 is a view of the system of FIG. 9 when the retaining element is in its second position.

FIG. 10 shows a view of the system of FIG. 9 when the retaining element 60 is in its second position. As shown in FIG. 10, fastener 40 has been fully inserted into hole 22 of stratum 20. Accordingly, the first blocking portion 61 partially overlaps the first hole 22 and thereby partially covers the head of the fastener 40 so as to prevent inadvertent backing out of the fastener 40. Further, as shown in FIG. 10, when the retaining element 60 is in its second position, the first cut-out 64 engages the spring element 30 so as to help maintain the retaining element 60 in its second position.

Parts of the retaining mechanism 100 may have a variety of shapes and sizes and still accomplish the functions described herein. For example, as shown, although the spring element 30 has a rectangular shape, a variety of shapes may be employed. For example, a more arcuate shape may be employed. Further, a different shape and/or type of spring than that shown may be employed. That is, as the spring element 30 shown may be considered a type of leaf spring, another type of spring having a different shape may be used.

Similarly, the shape of the retaining element 60 or any of its constituent parts may be different than that shown in the Figures as long as they accomplish their respective functions described herein. The retaining element 60 may any shape as long as it allows for insertion of fasteners and helps prevent inadvertent backing out of the fasteners after the fasteners have been fully inserted into the holes (for example, hole 22 or 22A). Further, although the tab 62 is shown as having a rectangular shape, a variety of shapes may be employed. As yet another example, although the depression 68 is shown as having a conical shape, a variety of shapes—for example, a spherical shape—may be employed.

In the embodiments shown and described herein, the retaining element 60 is substantially rigid. Further, in the embodiments shown and described herein, the stratum 20 is substantially rigid; accordingly, the channel 50 therein is substantially rigid.

The term "substantially" as used herein may be applied to modify any quantitative representation which could permissibly vary without resulting in a change in the basic function to which it is related. For example, the retaining element 60 may be considered substantially rigid if when the retaining element 60 is in its second position, the retaining element 60 at least partially overlaps a hole 22 or 22A so as to help prevent inadvertent backing out of a fastener after the fastener has been fully inserted into the hole.

In the embodiments described herein, the stratum may be made of a variety of biocompatible materials (metal or non-metal), including but not limited to, Titanium Alloys, commercially available Titanium, stainless steel, polyetheretherketone ("PEEK"), cobalt chrome ("CoCr"), polyetherketoneketone ("PEKK"), ultra high molecular weight polyethylene ("UHMWPE"), polyethylene, shape memory metals, other polymers or any combination of such materials. Similarly, the retaining mechanism 60 and/or the fasteners (for example, fastener 40) may be made of the same materials. Also, any suitable materials know in the art may work for each of these elements as well as for other elements described herein.

In the embodiments shown, the spring element 30 has elastic properties. Thus, the spring element 30 comprises a material that has elastic properties. For example, the spring element 30 may comprise a material such as metal that is elastic. In addition, the spring element 30, for example, may be made of Nickel Titanium (NiTi), commercially pure Titanium, a Titanium alloy or any combination of such materials. Further, as noted, the spring element 30 may have shapes other than rectangular. That is, the spring element 30 may take any form that satisfies its function described herein, for example, being able to adequately engage with the retaining element 60 and the stratum 20 and being able to sufficiently maintain the retaining element 60 in its second position so as to not allow the fasteners (for example, fastener 40) to inadvertently back out of the stratum 20.

All adjustments and alternatives described above are intended to be included within the scope of the invention, as defined exclusively in the following claims. Those skilled in the art also should realize that such modifications and equivalent constructions or methods do not depart from the spirit and scope of the present disclosure, and that they may make various changes, substitutions, and alterations herein without departing from the spirit and scope of the present disclosure. Furthermore, as used herein, the terms components and modules may be interchanged. It is understood that all spatial references, such as "superior," "inferior," "anterior," "posterior," "outer," "inner," "upper," "underside," "top," "bottom," and "perimeter" are for illustrative purposes only and can be varied within the scope of the disclosure.

The invention claimed is:

1. A retaining mechanism for use in affixing a stratum to bone, the mechanism comprising:
    a stratum comprising a first surface, a second surface, and a hole extending between the first surface and the second surface, the hole having a central longitudinal axis that extends substantially perpendicular to the first surface and the second surface, wherein the second surface is configured to engage at least a portion of the bone;
    a retaining element comprising:
        a first position that permits a fastener to be passed through the hole, and
        a second position that at least partially overlaps the hole, the retaining element being configured to rotate from the first position to the second position; and
    a spring element configured to engage the stratum and the retaining element such that the spring element maintains the retaining element in its second position so as to prevent inadvertent backing out of the fastener after the fastener has been fully inserted into the hole.

2. The mechanism of claim 1, wherein the stratum is further configured to engage the retaining element.

3. The mechanism of claim 1, wherein the spring element has a substantially linear configuration.

4. The mechanism of claim 1, wherein the stratum is substantially rigid.

5. The mechanism of claim 1, wherein the first surface of the stratum comprises a first recess configured to engage the retaining element.

6. The mechanism of claim 5, wherein the first recess comprises a second recess configured for disposal of the spring element.

7. The mechanism of claim 1, wherein:
    the retaining element further comprises a first leg and a second leg such that when the retaining element is in its second position, a portion of the first leg or a portion of the second leg partially overlaps the hole.

8. A system for affixing a stratum to bone, the system comprising:
    the retaining mechanism recited in claim 1; and
    a fastener configured to pass through the hole and engage the bone.

9. The mechanism of claim 1, wherein the spring element comprises material having elastic properties.

10. The mechanism of claim 1, wherein the spring element comprises Nickel Titanium or other Titanium alloy.

11. The mechanism of claim 1, wherein the retaining element comprises a central shaft configured to pass through a central hole in the stratum, the central shaft situated at or near a center of the retaining element, the retaining element comprising a tab and the stratum comprising a channel, the tab being movably disposed in the channel such that the retaining element is in its first position when the tab is positioned adjacent a first end of the channel and the retaining element is in its second position when the tab is positioned adjacent a second end of the channel.

12. The mechanism of claim 11, wherein the tab is spaced apart from the central shaft.

13. The mechanism of claim 1, wherein a first recess configured to engage the retaining element extends into the first surface, the first recess comprising a second recess configured for disposal of the spring element, the second recess extending into the first recess without extending through the second surface.

14. A retaining mechanism for use in affixing a stratum to bone, the mechanism comprising:
    a stratum comprising a first surface, a second surface, and a hole extending between the first surface and the second surface, the second surface situated in a first plane, wherein the second surface is configured to engage at least a portion of the bone, and
    a retaining element comprising:
        a first position that permits a fastener to be passed through the hole; and
        a second position that at least partially overlaps the hole, the retaining element being configured to rotate from the first position to the second position; and
    a spring element configured to engage the stratum and the retaining element such that the spring element maintains the retaining element in its second position so as to prevent inadvertent backing out of the fastener after the fastener has been fully inserted into the hole.

15. The mechanism of claim 14, wherein the retaining element comprises a central shaft configured to pass through a central hole in the stratum, the central shaft situated at or near a center of the retaining element, the retaining element further comprising a tab that is spaced apart from the central shaft, the stratum comprising a channel, the tab being movably disposed in the channel such that the retaining element is in its first position when the tab is positioned adjacent a first end of the channel and the retaining element is in its second position when the tab is positioned adjacent a second end of the channel.

16. The mechanism of claim 15, wherein the channel extends in a direction that is perpendicular to an axis defined by the hole.

17. A system for affixing a stratum to bone, the system comprising:

the retaining mechanism recited in claim 14; and a fastener configured to pass through the hole and engage the bone.

18. The mechanism of claim 14, wherein a first recess configured to engage the retaining element extends into the first surface, the first recess comprising a second recess configured for disposal of the spring element, the second recess extending into the first recess without extending through the second surface.

19. A retaining mechanism for use in affixing a stratum to bone, the mechanism comprising:

a stratum comprising a first surface, a second surface, and a hole extending between the first surface and the second surface, wherein the first surface is configured to engage at least a portion of the bone and the second surface defines a first recess having a depth, the first recess defining a second recess;

a retaining element disposed in the first recess comprising:
  a first position that permits a fastener to be passed through the hole;
  a second position that at least partially overlaps the hole, the retaining element being configured to rotate from the first position to the second position;
  a first leg and a second leg, both legs being situated in a first plane; and
  a tab configured to engage the stratum; and a spring element disposed in the second recess configured to engage the retaining element to maintain the retaining element in its second position so as to prevent inadvertent backing out of the fastener after the fastener has been fully inserted into the hole.

20. The mechanism of claim 19, wherein:

the stratum further comprises a central hole extending through the first and second surfaces; and the retaining element includes a central shaft configured for disposal in the central hole to allow the retaining element to rotate relative to the stratum about a longitudinal axis that extends parallel to the central hole, the central shaft being situated at or near a center of the retaining element.

* * * * *